US 8,470,602 B2
Jun. 25, 2013

(12) United States Patent
Chandler et al.

(54) METHODS AND SYSTEMS FOR DETERMINING THE PRESENCE OR AMOUNT OF DELTA 5 STEROID COMPOUNDS IN A SAMPLE

(75) Inventors: Donald Walt Chandler, Agoura Hills, CA (US); Russell Philip Grant, Chapel Hill, NC (US); Samuel Meares, Burlington, NC (US); Patricia Holland, High Point, NC (US)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

(21) Appl. No.: 13/368,164

(22) Filed: Feb. 7, 2012

(65) Prior Publication Data

US 2012/0270327 A1 Oct. 25, 2012

Related U.S. Application Data

(60) Provisional application No. 61/440,282, filed on Feb. 7, 2011.

(51) Int. Cl.
| | | |
|---|---|---|
| G01N 33/74 | (2006.01) | |
| G01N 33/92 | (2006.01) | |
| G01N 27/62 | (2006.01) | |
| G01N 30/02 | (2006.01) | |

(52) U.S. Cl.
USPC ............ 436/71; 436/63; 436/128; 436/131; 436/161; 436/173; 436/174; 436/175; 422/70; 422/78; 250/281; 250/282

(58) Field of Classification Search
USPC ............ 436/56, 63, 71, 127, 128, 131, 161, 436/173, 174, 175; 422/68.1, 69, 70, 78; 250/281, 282; 210/656, 198.2
See application file for complete search history.

(56) References Cited

U.S. PATENT DOCUMENTS

| | | | |
|---|---|---|---|
| 3,026,320 A | 3/1962 | Djerassi et al. | |
| 6,930,192 B2 | 8/2005 | Dalko et al. | |
| 6,977,143 B1 * | 12/2005 | Caulfield et al. | 435/4 |
| 7,473,560 B2 * | 1/2009 | Soldin | 436/173 |
| 7,804,063 B2 * | 9/2010 | Ghoshal et al. | 250/282 |
| 7,935,921 B2 * | 5/2011 | Grant et al. | 250/288 |
| 2009/0134325 A1 * | 5/2009 | Goldman et al. | 250/283 |
| 2009/0155766 A1 * | 6/2009 | Goldman et al. | 435/4 |
| 2009/0312299 A1 | 12/2009 | Tuba et al. | |
| 2010/0059671 A1 * | 3/2010 | Ghoshal et al. | 250/282 |
| 2011/0003395 A1 | 1/2011 | Dey et al. | |

OTHER PUBLICATIONS

International Search Report for PCT/US12/24187, dated May 18, 2012.

* cited by examiner

*Primary Examiner* — Maureen Wallenhorst
(74) *Attorney, Agent, or Firm* — Kilpatrick Townsend & Stockton, LLP (57) ABSTRACT

Disclosed are methods and systems for the analysis of delta 5 steroid compounds in a sample using supported liquid extraction and liquid chromatography/mass spectrometry.

24 Claims, 4 Drawing Sheets

METHODS AND SYSTEMS FOR DETERMINING THE PRESENCE OR AMOUNT OF DELTA 5 STEROID COMPOUNDS IN A SAMPLE

CROSS-REFERENCE TO RELATED APPLICATIONS

The present application claims the benefit of priority of U.S. Provisional Patent Application No. 61/440,282, filed Feb. 7, 2011, which is incorporated by reference as though fully set forth herein.

FIELD OF INVENTION

The present invention provides methods and systems for determining the presence or amount of a biomarker in a sample. In particular, the invention provides methods and systems for analyzing delta 5 steroids in a sample using liquid chromatography and mass spectrometry.

BACKGROUND

Biomarkers, such as hormones, vitamins, and/or metabolites, can be used for the clinical diagnosis of multiple disorders and as endogenous biomarkers in endocrinology. Steroid hormones, such as delta 5 steroids, are an important class of hormones.

Requirements for the clinical diagnostic testing of endogenous biomarkers in endocrinology may include highly sensitive and specific assays, the ability to analyze small sample volumes (e.g., pediatric sample volumes can be limited to less than about 200 µL), and the ability to screen for multiple analytes to accurately diagnose a disease state, e.g., an endocrine disorder. Historically, radioimmunoassay (RIA) and enzyme-linked immunoassay (ELISA) methods have been used in such clinical diagnostic testing. Immunoassay methods (IA), such as RIA and EIA, however, may suffer from low throughput, antibody cross-reactivity, which can require extra preparation for specificity, and poor scalability. Also, the analysis of endogenous biomarkers by RIA may require multiple serial dilutions for the analysis of each individual marker, which can lead to the need to make multiple adjustments to normalize sample volumes and/or the need for multiple separate tests. Also, immunoassay testing is not particularly conducive to the analysis of multiple biomarkers in each sample. The analysis for multiple analytes in a single assay can allow for using samples of reduced size which results in assays of increased sensitivity and efficiency per sample.

Thus, there is a need to develop analytical techniques that can be used for the measurement of endogenous biomarkers, and for methods that provide more sensitivity and higher throughput than RIA. Until recently, however, only GC-MS or LC-MS/MS with derivatization has been successful for small sample volumes. Thus, there is a need in the art for LC-MS/MS techniques for the analysis of endogenous biomarkers for clinical diagnosis in endocrinology capable of providing detection limits at acceptable levels, without the need for the cumbersome derivatization processes.

SUMMARY OF THE INVENTION

In at least one aspect, the invention provides methods for determining the presence or amount of a delta 5 steroid compound in a sample, the method comprising: (a) providing a sample containing a delta 5 steroid compound and one or more delta 4 steroid compounds; (b) oxidizing the one or more delta 4 steroid compounds in the sample using an oxidizing agent; (c) chromatographically separating the delta 5 steroid compound from other components in the oxidized sample using liquid chromatography; and (d) analyzing the chromatographically separated delta 5 steroid compound by mass spectrometry to determine the presence or amount of the delta 5 steroid compound in the sample. Further embodiments of these methods are described in detail below.

In another aspect, the invention provides methods for determining the amount of a delta 5 steroid compound in a sample, the method comprising: (a) providing a sample containing a delta-5 steroid compound and one or more delta 4 steroid compounds; (b) oxidizing the one or more delta 4 steroid compounds in the sample using an oxidizing agent; (c) chromatographically separating the delta 5 steroid compound from the other components in the oxidized sample using reverse phase liquid chromatography; and (d) analyzing the chromatographically separated delta 5 steroid compound by mass spectrometry to determine the amount of the delta 5 steroid compound in the sample. Further embodiments of these methods are described in detail below.

In another aspect, the invention provides methods of generating a report useful for diagnosing a disease or condition associated with abnormal delta 5 steroid levels, the method comprising: (a) providing a sample containing a delta 5 steroid compound and one or more delta 4 steroid compounds; (b) oxidizing the one or more delta 4 steroid compounds in the sample using an oxidizing agent; (c) chromatographically separating the delta 5 steroid compound from other components in the oxidized sample using liquid chromatography; (d) analyzing the chromatographically separated delta 5 steroid compound by mass spectrometry to determine the presence or amount of the delta 5 steroid compound in the sample; and (e) generating a report that recites the concentration of a delta 5 steroid compound in the biological sample. Further embodiments of these methods are described in detail below.

In another aspect, the invention provides systems for determining the presence or amount of a delta 5 steroid compound in a sample, the system comprising: (a) a station for oxidizing a sample, the sample comprising a delta 5 steroid compound and one or more delta 4 steroid compounds; (b) a station for chromatographically separating the delta 5 steroid compound from other components in the oxidized sample using liquid chromatography; and (c) a station for analyzing the chromatographically separated delta 5 steroid compound by mass spectrometry to determine the presence or amount of the delta 5 steroid compound in the sample. Further embodiments of these methods are described in detail below.

Further aspects of the invention are described in detail below.

DETAILED DESCRIPTION

Figure 1:
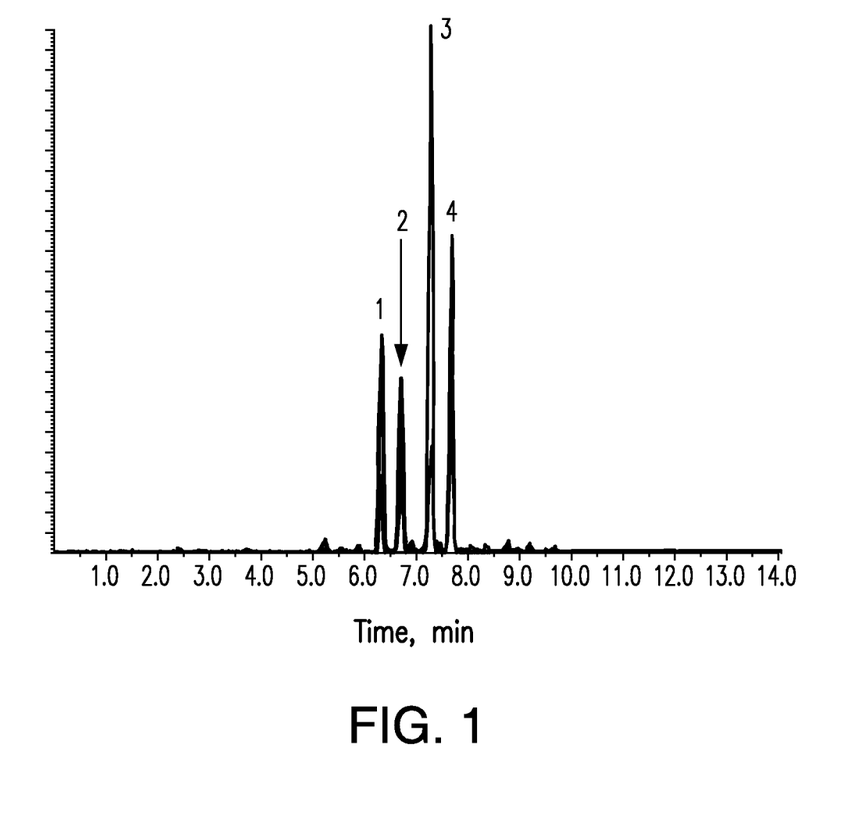
FIG. 1 shows the result for the separation and analysis of DHEA by the method of Example 1 except that no oxidation is performed. Extraction was performed with 50:50 (v/v) hexane and ethyl acetate. The peak for DHEA (Peak 2) was recorded at 6.72 minutes. Intensity was measured as $2.0 \times 10^5$ cps. Peaks 1, 3, and 4 are for other species, and occur at 6.32 minutes, 7.29 minutes, and 7.68 minutes, respectively.
Figure 2:
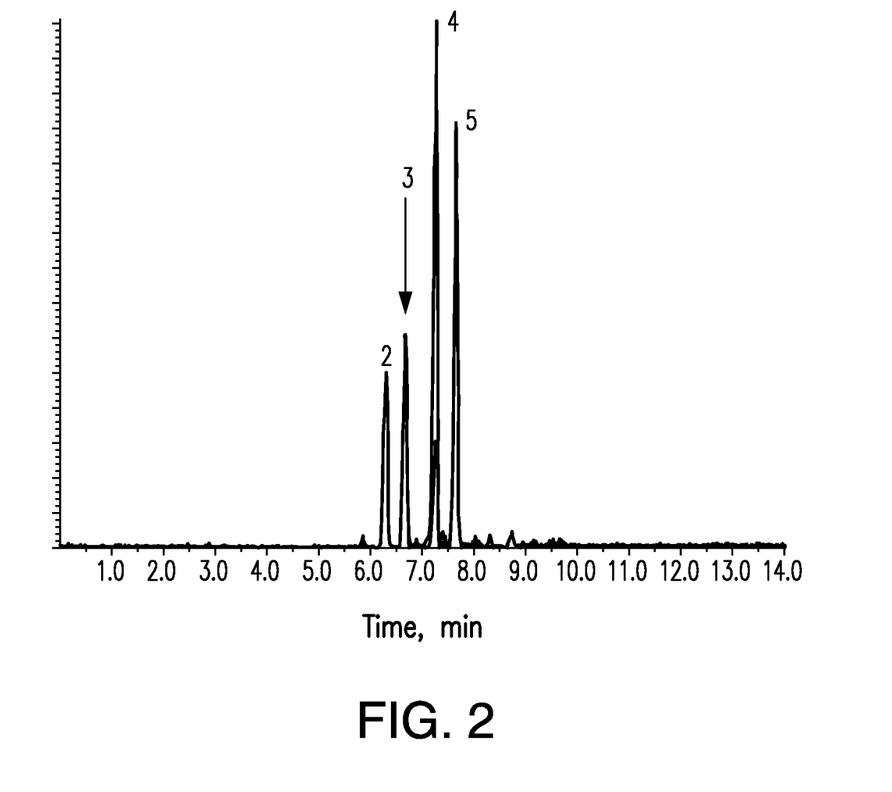
FIG. 2 shows the result for the separation and analysis of DHEA by the method of Example 1 except that no oxidation is performed. Extraction was performed with 99:1 (v/v) hexane and ethyl acetate. The peak for DHEA (Peak 3) was recorded at 6.70 minutes. Intensity was measured as $1.6 \times 10^5$ cps. Peaks 1, 2, 4, and 5 are for other species, and occur at 5.85 minutes, 6.29 minutes, 7.26 minutes, and 7.66 minutes, respectively.
Figure 3:
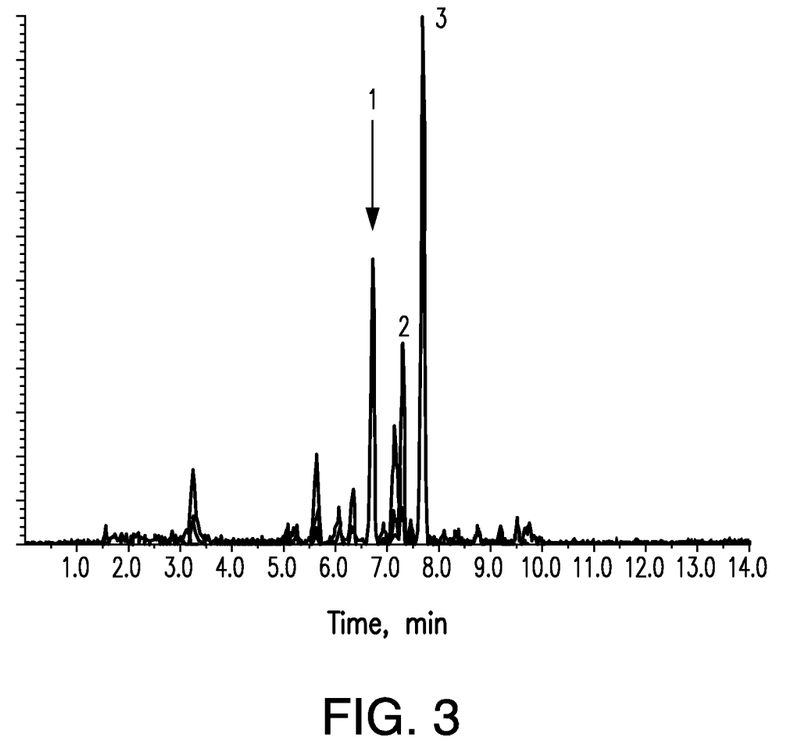
FIG. 3 shows the result for the separation and analysis of DHEA by the method of Example 1. Extraction was performed with 50:50 (v/v) hexane and ethyl acetate with 1% $KMnO_4$. The peak for DHEA (Peak 1) was recorded at 6.72 minutes. Intensity was measured as $1.6 \times 10^5$ cps. Peaks 2 and 3 are for other species, and occur at 7.29 minutes and 7.69 minutes, respectively.
Figure 4:
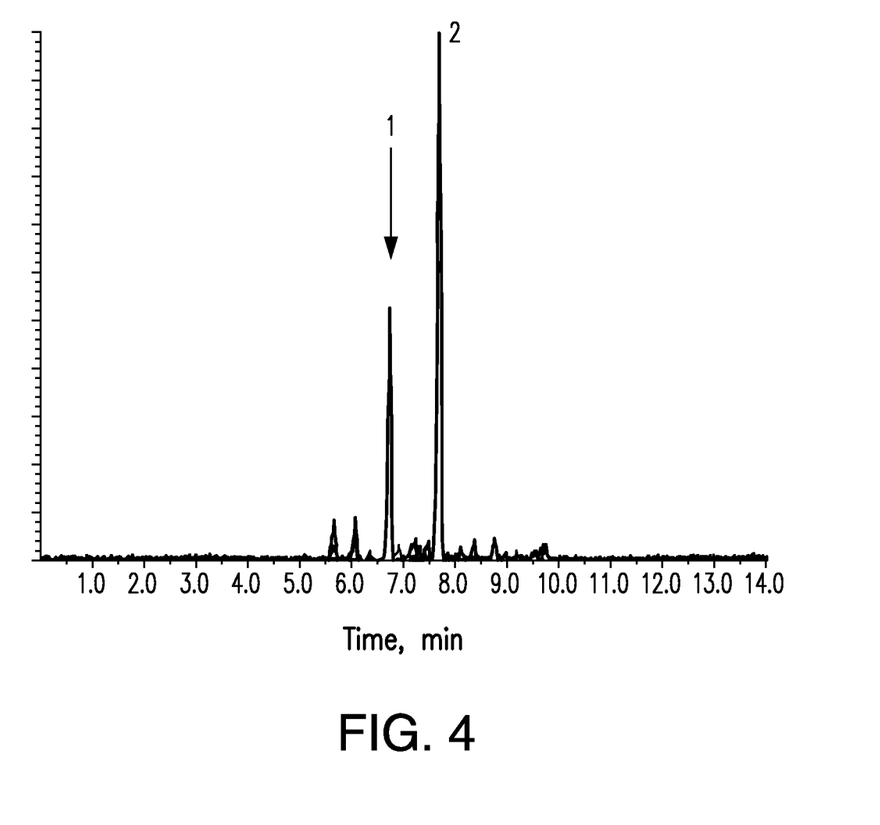
FIG. 4 shows the result for the separation and analysis of DHEA by the method of Example 1. Extraction was performed with 99:1 (v/v) hexane and ethyl acetate. The peak for DHEA (Peak 1) was recorded at 6.72 minutes. Intensity was measured as $1.2 \times 10^5$ cps. Peak 2 is for another species, and occurs at 7.69 minutes.

The following description recites various aspects and embodiments of the present invention. No particular embodiment is intended to define the scope of the invention. Rather, the embodiments merely provide non-limiting examples various methods and systems that are at least included within the scope of the invention. The description is to be read from the perspective of one of ordinary skill in the art; therefore, information well known to the skilled artisan is not necessarily included.

Various abbreviations may be used in the application. In most, if not all, instances, the meanings of such abbreviations are known to those of skill in the art. These abbreviations include the following abbreviations, whose meanings are provided.

| | |
|---|---|
| APCI = | atmospheric pressure chemical ionization |
| CBP = | competitive binding protein |
| HTLC = | high turbulence (throughput) liquid chromatography |
| HPLC = | high performance liquid chromatography |
| LLE = | liquid-liquid extraction |
| LOQ = | limits of quantification |
| LLOQ = | lower limit of quantification |
| IA = | immunoassay |
| ELISA = | enzyme linked immunoassay |
| RIA = | radioimmunoassay |
| SST = | system suitability test |
| ULOQ = | upper limit of quantification |
| 2D-LC-MS/MS = | two-dimensional liquid chromatography hyphenated to tandem mass spectrometry |
| (LC)-LC-MS/MS = | two-dimensional liquid chromatography tandem hyphenated to mass spectrometry |
| (LC)-MS/MS = | liquid chromatography hyphenated to tandem mass spectrometry |
| SLE = | supported liquid extraction |

Definitions

The following terms, unless otherwise indicated, shall be understood to have the following meanings:

As used herein, the terms "a," "an," and "the" can refer to one or more unless specifically noted otherwise.

As used herein, the term "biomarker" is any biomolecule that may provide biological information about the physiological state of an organism. In certain embodiments, the presence or absence of the biomarker may be informative. In other embodiments, the level of the biomarker may be informative. A biomarker may be a hormone, such as a delta 5 steroid compound, or a metabolite of a hormone.

As used herein, the term "steroid compound" refers to a compound that has the basic fused ring structure of gonane, without respect to saturation or stereochemistry. The three six-membered rings in the core structure are referred to as the "A ring", the "B ring" and the "C ring". The 5-membered ring is referred to as the "D ring", with the A ring being farthest from the D ring, and the B ring being next farthest from the D ring. The carbon atoms on the steroid compound are numbered according to the traditional manner of numbering carbon atoms on steroid compounds.

As used herein, the term "delta 4 steroid compound" refers to a steroid compound having a double bond in the A ring between the 4 and 5 carbons of the steroidal core. Testosterone is an example of a delta 4 steroid compound.

As used herein, the term "delta 5 steroid compound" refers to a steroid compound having a double bond in the B ring between the 5 and 6 carbons of the steroidal core. Pregnenolone is an example of a delta 5 steroid compound.

Throughout this application, the term "about" is used to indicate that a value includes the inherent variation of error for the device, the method being employed to determine the value, or the variation that exists among the study subjects.

As used herein, the terms "subject," "individual," and "patient" are used interchangeably. The use of these terms does not imply any kind of relationship to a medical professional, such as a physician.

As used herein, the phrase "liquid chromatography" or "LC" is used to refer to a process for the separation of one or more molecules or analytes in a sample from other analytes in the sample. LC involves the slowing of one or more analytes of a fluid solution as the fluid uniformly moves through a column of a finely divided substance. The slowing results from the distribution of the components of the mixture between one or more stationery phases and the mobile phase. LC includes, for example, reverse phase liquid chromatography (RPLC) and high pressure liquid chromatography (HPLC).

As used herein, the term "separate" or "purify" or the like are not used necessarily to refer to the removal of all materials other than the analyte of interest from a sample matrix. Instead, in some embodiments, the terms are used to refer to a procedure that enriches the amount of one or more analytes of interest relative to one or more other components present in the sample matrix. In some embodiments, a "separation" or "purification" may be used to remove or decrease the amount of one or more components from a sample that could interfere with the detection of the analyte, for example, by mass spectrometry.

As used herein, the term "mass spectrometry" or "MS" analysis refers to a technique for the identification and/or quantitation of molecules in a sample. MS includes ionizing the molecules in a sample, forming charged molecules; separating the charged molecules according to their mass-to-charge ratio; and detecting the charged molecules. MS allows for both the qualitative and quantitative detection of molecules in a sample. The molecules may be ionized and detected by any suitable means known to one of skill in the art. The phrase "tandem mass spectrometry" or "MS/MS" is used herein to refer to a technique for the identification and/or quantitation of molecules in a sample, wherein multiple rounds of mass spectrometry occur, either simultaneously using more than one mass analyzer or sequentially using a single mass analyzer. As used herein, a "mass spectrometer" is an apparatus that includes a means for ionizing molecules and detecting charged molecules.

As used herein, "electrospray ionization" or "ESI" refers to a technique used in mass spectrometry to ionize molecules in a sample while avoiding fragmentation of the molecules. The sample is dispersed by the electrospray into a fine aerosol.

The sample will typically be mixed with a solvent, usually a volatile organic compound (e.g., methanol or acetonitrile) mixed with water. The aerosol is then transferred to the mass spectrometer through a capillary, which can be heated to aid further solvent evaporation from the charged droplets.

As used herein, a "quadrupole analyzer" is a type of mass analyzer used in MS. It consists of four circular rods (two pairs) that are set highly parallel to each other. The quadrupole analyzer is the component of the instrument that organizes the charged particles of the sample based on their mass-to-charge ratio. One of skill in the art would understand that use of a quadrupole analyzer can lead to increased specificity of results. One pair of rods is set at a positive electrical potential and the other set of rods is at a negative potential. To be detected, an ion must pass through the center of a trajectory path bordered and parallel to the aligned rods. When the quadrupoles are operated at a given amplitude of direct current and radio frequency voltages, only ions of a given mass-to-charge ratio will resonate and have a stable trajectory to pass through the quadrupole and be detected. As used herein, "positive ion mode" refers to a mode wherein positively charged ions are detected by the mass analyzer, and "negative ion mode" refers to a mode wherein negatively charged ions are detected by the mass analyzer. For "selected ion monitoring" or "SIM," the amplitude of the direct current and the radio frequency voltages are set to observe only a specific mass.

As used herein, the term "analytical column" refers to a chromatography column having sufficient chromatographic plates to effect a separation of the components of a test sample matrix. Preferably, the components eluted from the analytical column are separated in such a way to allow the presence or amount of an analyte(s) of interest to be determined. In some embodiments, the analytical column comprises particles having an average diameter of about 5 μm. In some embodiments, the analytical column is a functionalized silica or polymer-silica hybrid, or a polymeric particle or monolithic silica stationary phase, such as a phenyl-hexyl functionalized analytical column.

Analytical columns can be distinguished from "extraction columns," which typically are used to separate or extract retained materials from non-retained materials to obtained a "purified" sample for further purification or analysis. In some embodiments, the extraction column is a functionalized silica or polymer-silica hybrid or polymeric particle or monolithic silica stationary phase, such as a Poroshell SBC-18 column.

The term "heart-cutting" refers to the selection of a region of interest in a chromatogram and subjecting the analytes eluting within that region of interest to a second separation, e.g., a separation in a second dimension.

As used herein, the term "hemolysed" refers to the rupturing of the red blood cell membrane, which results in the release of hemoglobin and other cellular contents into the plasma or serum and the term "lipemic" refers to an excess of fats or lipids in blood.

Methods for Determining the Presence or Amount of Delta 5 Steroid Compound

In at least one aspect, the invention provides methods for determining the presence or amount of a delta 5 steroid compound in a sample, the method comprising: (a) providing a sample containing a delta 5 steroid compound and one or more delta 4 steroid compounds; (b) oxidizing the one or more delta 4 steroid compounds in the sample using an oxidizing agent; (c) chromatographically separating the delta 5 steroid compound from other components in the oxidized sample using liquid chromatography; and (d) analyzing the chromatographically separated delta 5 steroid compound by mass spectrometry to determine the presence or amount of the delta 5 steroid compound in the sample.

These methods comprise providing a sample containing a delta 5 steroid compound. In this context, the term "providing" is to be construed broadly. The term is not intended to refer exclusively to a subject who provided a biological sample. For example, a technician in an off-site clinical laboratory can be said to "provide" the sample, for example, as the sample is prepared for oxidation and/or purification by chromatography.

The sample is not limited to any particular sample type. The sample contains a delta 5 steroid compound, but, in general, also includes other components, for example, one or more delta 4 steroid compounds. In some embodiments, the sample is a sample that has been processed and prepared for oxidation and/or purification by chromatography. Such processing may be useful for optimizing the effectiveness of subsequent purification steps. Such processing methods are well known to those of skill in the art.

The invention is not limited to any particular means of sample handling. In some embodiments, it may be useful to separate the sample into two or more fractions prior to purification by extraction and/or chromatography. In some such embodiments, two or more of such fractions may be prepared differently, for example, to help improve the sensitivity or selectivity of the separation for a particular column chemistry. In some embodiments, the method includes preparing a single sample for repeat injections across multiple liquid chromatography systems.

The invention is not limited to any particular sample size. In some embodiments, the sample comprises a biological sample. In such embodiments, the sample may also include other components, such as solvents, buffers, anticlotting agents and the like. In embodiments where the sample comprises a biological sample, the biological sample can be one or more of whole blood, plasma, serum, urine, cerebrospinal fluid, tissue homogenate, saliva, amniotic fluid, bile, mucus, peritoneal fluid, or lymphatic fluid. The invention is not limited to any particular volume of biological sample. In some embodiments, the biological sample is at least about 25-250 μL, at least about 35-200 μL, at least about 45-150 μL, or at least about 50-100 μL in volume. In certain embodiments, the biological sample is at least about 60 μL in volume.

The sample comprises a delta 5 steroid compound. The methods may be used to analyze any suitable delta 5 steroid compound. In some embodiments, the delta 5 steroid compound is pregnenolone, 17α-hydroxy-pregnenolone, or 5-dehydroepiandrosterone (DHEA). In some embodiments, the sample comprises one or more of 17α-hydroxy-pregnenolone, and DHEA.

In some embodiments, the sample also comprises delta 4 steroid compounds. In some embodiments, the delta 4 steroid compound is a conjugated delta 4 steroid compound, meaning that the delta 4 steroid compound has a carbonyl group at the 3-position on the steroidal core, such that the double bond at the 4 position is conjugated with the carbonyl double bond. In some embodiments, the one or more delta 4 steroid compounds independently are cortisol, 21-deoxycortisol, dexamethasone, corticosterone, beclomethasone, 11-desoxycortisol, triamcinolone acetonide, tetrahydrocortisol, 11-α-hydroxyprogesterone, tetrahydrocortisone, 19-nortestosterone, androstenedione, estradiol, estrone, 17a-ethynylestradiol, deoxycorticosterone, testosterone, 17α-hydroxyprogesterone, 17β-dihydroepiandrosterone, 17α methyltestosterone, budesonide, epiandrosterone, epitestosterone, dihydrotestosterone, dehydroandrosterone, fluticasone propionate, 20α-dihydroprogesterone, dihydroandrosterone, progesterone, 5α-androstan-3α-ol-17-one, 20β-hydroxyprogesterone, beclomethasone dipropionate, 5β-pregnane-3a,17a,20a-triol, pregnanolone, etiocholan-3α-diol, estriol, aldosterone, prednisone, cortisone, adrenosterone, 5α-androstan-3,11,17-trione, prednisolone, or pregnanediol.

The method further comprises oxidizing the sample using an oxidizing agent. In some embodiments, the oxidizing preferentially oxidizes the delta 4 steroid compounds relative to the delta 5 steroid compounds. In some embodiments, this oxidation of the delta 4 steroid compounds changes their molecular structure so that they have a different molecular weight, and/or fragment differently in a mass spectrometer, and/or generate fragment ions that have different molecular weights. In some embodiments, this can reduce the degree to which delta 4 steroid compounds present in the sample interfere with the analysis of delta 5 steroid compounds by mass spectrometry.

The invention is not limited to any particular method of performing the oxidation. Any suitable method can be used, so long as it brings the oxidizing agent into contact with the delta 4 steroid compounds in the sample. In some embodiments, the oxidizing includes partitioning the delta 5 steroid compound and the delta 4 steroid compounds between an aqueous phase and an organic phase, for example, by liquid-liquid extraction (LLE). In some such embodiments, at least the aqueous phase comprises an amount of an oxidizing agent.

The invention is not limited to the use of any particular oxidizing agent. Any suitable oxidizing agent can be used. In some embodiments, the oxidizing agent is permanganate ion, chromate ion, osmium tetroxide, perchlorate ion, periodate ion, or any mixture of two or more of the foregoing. In some embodiments, the oxidizing agent is permanganate ion. In such embodiments, potassium permanganate can be the source of the permanganate ion.

In embodiments that employ LLE to carry out the oxidation, the organic phase can include any suitable non-polar solvent system. In some embodiments, the organic phase comprises a organic water-immiscible solvent system. Such solvents systems are well known in the art. The organic water-immiscible solvent system includes, but is not limited to ethyl acetate, hexane, toluene, octanol, cholroform, dichloromethane, cyclohexane, pentane, N-heptanes, benzene, n-butyl chloride, butanol, methylene chloride, and mixtures of any two or more of the foregoing. In some embodiments, the organic water-immiscible solvent system can also include some amount of one or more polar solvents. In such embodiments, the amount of polar solvent must be sufficiently low to ensure that the solvent system remains generally water immiscible. Suitable polar solvents for use in such embodiments include, but are not limited to methanol, acetone, acetonitrile, isopropanol, diethyl ether, or methyl-t-butyl ether.

The LLE can be carried out using any suitable apparatus designed therefor. Suitable apparatuses are well known in the art. Further, the oxidizing step can, in some embodiments, be accompanied by applying mechanical action to the LLE apparatus to facilitate oxidation. Such mechanical action can include agitation, vibration, and the like.

In some embodiments of the invention, the oxidized sample can undergo one or more processing steps before chromatographic separation. For example, in some embodiments, the oxidized sample is evaporated. Then, the resulting residue is reconstituted in a solvent system. Any suitable solvent system can be used for reconstituting the residue. In some embodiments, the solvent system is a solvent system that is compatible with chromatographic separation. In some embodiments, the solvent system for reconstitution includes, but is not limited to, water, methanol, or mixtures thereof.

The methods comprise chromatographically separating a delta 5 steroid compound using liquid chromatography. The invention is not limited to any particular manner of performing liquid chromatography. In general, the chromatographic separation step includes using at least one liquid chromatography (LC) column. In some embodiments, multiple LC columns are used, such as two or more, or three or more, or four or more LC columns. In some such embodiments two, three, four, five, six, eight, or ten LC columns are used. In some such embodiments, two or more of these LC columns are arranged parallel to each other, and are connected inline to the same mass spectrometer.

The invention is not limited to any particular types of columns. Any column suitable for the separation of a delta 5 steroid compound can be used. In some embodiments, one or more analytical columns are used. In some such embodiments, one or more reverse phase columns are used. In some embodiments, the method employs two or more reverse phase columns in parallel, which are connected inline to the same mass spectrometer.

Further, the invention is not limited to any particular mobile phase. Any suitable mobile phase can be used, as long as the mobile phase is suitable for use with a particular LC column and for chromatographically separating the delta-5 steroid compound in the LC column. In some embodiments, the mobile phase is a polar solvent system. The polar solvent system can include one or more polar solvents, including but not limited to water, methanol, acetonitrile, or a mixture of two or more of the foregoing. In some such embodiments, the mobile phase employs a gradient, such that the relative ratios of two or more solvents are varied over time.

As noted above, two or more LC columns (e.g., reverse phase columns) can be used in parallel and connected inline to the same mass spectrometer, e.g., to improve throughput. In some such embodiments, a delta 5 steroid compound-containing sample (i.e., the partially purified sample, e.g., following evaporation and reconstitution) is introduced to the two or more LC columns at different times. In some embodiments, the introduction of the test sample to the two or more LC columns is staggered, meaning that there is a pre-determined time interval separating the introduction of sample to two or more LC columns. Appropriate time intervals can be selected based on various factors, including the elution time, column chemistries, and the potential need to avoid interfering with the analysis of the delta 5 steroid compound eluted from one or more of the other LC columns.

In some embodiments of the invention, another LC column can be placed in series with another column. For example, in some embodiments, suitable guard columns can be employed. Those of skill in the art are able to select appropriate guard columns for use in the present methods. In some embodiments, a guard column is placed in parallel with another LC column, and both the guard column and the LC column are reverse phase columns. Such series of two or more columns can also be arranged in parallel, such that there are two or more series of columns operating in parallel, where each series contains two or more columns.

The methods comprise analyzing the chromatographically separated delta 5 steroid compound by mass spectrometry to determine the presence or amount of the delta 5 steroid compound. In some embodiments, two or more of the LC columns feed into the same mass spectrometer. In some further embodiments, three or more of the LC columns feed into the same mass spectrometer. In some embodiments, the mass spectrometer is part of a combined LC-MS system.

The invention is not limited to any particular type of mass spectrometer. Any suitable mass spectrometer can be used. In some embodiments, the method employs a tandem mass spectrometer. In some such embodiments, analyzing the delta 5 steroid compound can include, ionizing the delta 5 steroid compound, analyzing the ionized the delta 5 steroid compound, fragmenting the delta 5 steroid compound ion into two or more fragment ions, and analyzing the fragment ions. The invention is not limited to a mass spectrometer using any particular ionization methods. Any suitable ionization can be used. Suitable ionization methods include, but are not limited to photoionization, electrospray ionization, atmospheric pressure chemical ionization, and electron capture ionization. And in embodiments that employ fragmenting, any suitable fragmentation technique can be used. Suitable techniques include, but are not limited to collision induced dissociation, electron capture dissociation, electron transfer dissociation, infrared multiphoton dissociation, radiative dissociation, electron-detachment dissociation, and surface-induced dissociation.

In some embodiments, the tandem mass spectrometer is a MDS-Sciex API5000 triple quadrupole mass spectrometer. In some embodiments, the tandem mass spectrometer has an atmospheric pressure ionization source, and the analyzing step comprises an ionization method selected from the group consisting of photoionization, electrospray ionization (ESI), atmospheric pressure chemical ionization (APCI), electron capture ionization, electron ionization, fast atom bombardment/liquid secondary ionization (FAB/LSI), matrix assisted laser desorption ionization (MALDI), field ionization, field desorption, thermospray/plasmaspray ionization, and particle beam ionization. The ionization method may be in positive ion mode or negative ion mode. The analyzing step may also include multiple reaction monitoring or selected ion monitoring (SIM), and the two or more biomolecules are analyzed simultaneously or sequentially. In some embodiments, the analyzing step uses a quadrupole analyzer. In some embodiments, the mass spectrometer is a triple quadrupole mass spectrometer.

The methods, in some embodiments, include using an internal standard. In such embodiments, the internal standard can be introduced at any suitable point prior to the chromatographic separation step. Any suitable internal standard can be used. In some embodiments, the internal standard is a stable isotopically-labeled delta 5 steroid compound. In some such embodiments, the internal standard is labeled by carbon-13 and/or deuterium. In some embodiments, the internal standard is $D_4$-pregnenolone, $D_3$-17-hydroxy-pregnenolone, or $D_6$-5-dehydroepiandrosterone.

In some embodiments, the amount of the delta 5 steroid compound need not be determined. In some embodiments, the method can be used to determine the presence or absence of the delta 5 steroid compound in a sample. In other embodiments, the method is used to determine the amount of the delta 5 steroid compound in a sample. For example, in some embodiments and/or aspects, the invention provides methods for determining the amount of a delta 5 steroid compound in a sample, the method comprising: (a) providing a sample containing a delta-5 steroid compound and one or more delta 4 steroid compounds; (b) oxidizing the one or more delta 4 steroid compounds in the sample using an oxidizing agent; (c) chromatographically separating the delta 5 steroid compound from the other components in the oxidized sample using reverse phase liquid chromatography; and (d) analyzing the chromatographically separated delta 5 steroid compound by mass spectrometry to determine the amount of the delta 5 steroid compound in the sample.

In some embodiments, the method is not limited by any lower-limit and/or upper-limit of detection. In some embodiments, the methods can be used to measure the delta 5 steroid compound in a sample (e.g., a sample comprising a biological sample) at concentrations that range from 2.5 ng/dL to 5000 ng/dL, or from 5 ng/dL to 5000 ng/dL, or from 10 ng/dL to 5000 ng/dL, or from 2.5 ng/dL to 2000 ng/dL.

Methods of Generating Reports

In another aspect, the invention provides methods of generating a report useful for diagnosing a disease or condition associated with abnormal delta 5 steroid levels, the method comprising: (a) providing a sample containing a delta 5 steroid compound and one or more delta 4 steroid compounds; (b) oxidizing the one or more delta 4 steroid compounds in the sample using an oxidizing agent; (c) chromatographically separating the delta 5 steroid compound from other components in the oxidized sample using liquid chromatography; (d) analyzing the chromatographically separated delta 5 steroid compound by mass spectrometry to determine the presence or amount of the delta 5 steroid compound in the sample; and (e) generating a report that recites the concentration of a delta 5 steroid compound in the biological sample.

The features and embodiments of all steps except step (e) are described immediately above. As noted above, the method can employ more than one column, e.g., two or more columns in parallel connected inline to the same mass spectrometer.

The method further includes generating a report that recites the amount of at least one the delta 5 steroid compound in the sample. In some embodiments, this information can be used to determine the concentration of the delta 5 steroid compound in a biological sample. From such information, one could assess whether a subject has an abnormally high or low amount of the delta 5 steroid compound.

Such information can be useful for diagnosing one or more diseases or disorders that may be associated with aberrant levels of the delta 5 steroid compound in a subject. Such diseases or conditions are well known in the art. Such diseases or conditions include, but are not limited to the following: cholesterol sidechain cleavage, 3β-hydroxysteroid dehydrogenase deficiency, carcinomas, and various disorders of the immune system.

Systems for Analyzing Biomolecules

In another aspect, the invention provides systems for determining the presence or amount of a delta 5 steroid compound in a sample, the system comprising: (a) a station for oxidizing a sample, the sample comprising a delta 5 steroid compound and one or more delta 4 steroid compounds; (b) a station for chromatographically separating the delta 5 steroid compound from other components in the oxidized sample using liquid chromatography; and (c) a station for analyzing the chromatographically separated delta 5 steroid compound by mass spectrometry to determine the presence or amount of the delta 5 steroid compound in the sample.

Such systems can include various embodiments and sub-embodiments analogous to those described above for methods of analyzing the delta 5 steroid compound.

These systems include various stations. As used herein, the term "station" is broadly defined and includes any suitable apparatus or collections of apparatuses suitable for carrying out the recited method. The stations need not be integrally connected or situated with respect to each other in any particular way. The invention includes any suitable arrangements of the stations with respect to each other. For example, the stations need not even be in the same room. But in some embodiments, the stations are connected to each other in an integral unit.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Analysis for Pregnenolone

Principle

Pregnenolone is measured by mass spectrometric detection after liquid-liquid extraction. Analysis is performed using liquid chromatography separation with tandem mass spectrometric detection (LC-MS/MS). Stable labeled isotopic pregnenolone is added as an internal standard to serum aliquots.

Samples are first extracted with 99.5:0.5 Hexane: Ethyl Acetate. The extract is then oxidized with a potassium permanganate solution to remove unwanted circulating delta-4 steroids and then evaporated and reconstituted. An MDS-Sciex API5000 triple quadrupole mass spectrometer, operating in positive ion atmospheric pressure chemical ionization (APCI) mode is used for detection. Quantification of analyte and internal standard is performed in selected reaction monitoring mode (SRM). The back-calculated amount of pregnenolone in each sample is determined from duplicate calibration curves generated by spiking known amounts of purified pregnenolone into charcoal stripped human serum from 10 to 2000 ng/dL.

Specimens

At least 0.4 mL of serum is collected from adult or pediatric humans. The recommended sample size is 1.0 mL. The samples are stored for up to 3 months at a temperature of −20° C. or lower. If shipped, the samples are shipped at a temperature of −70° C. or lower. Serum is separated from whole blood within 4 hours of collection. Stable isotopically labeled pregnenolone, Pregnenolone-17alpha, 21, 21, 21-$d_4$, CDN Isotopes, Catalog #D-5341 (Sigma-Aldrich) is used as an internal standard.

Equipment & Reagents & Preparation

The method employs the following equipment: Standard manual pipetting devices; Positive displacement dispensers, 1 mL-10 mL, with glass and Teflon parts; PARAFILM, (American National Can); Rotary Evaporator (rotovap), SpeedVac SC 200 (Savant); 1.2 mL MBlock Polypropylene 96-Well Collection Plate (SPE Ware, Inc. Product No. SPE0210); Heat Sealing Foil (SPE Ware, Inc. Product No. AB-0589); Mini-Vap 96-Well Plate Evaporator, Porvair, Inc (USA); Mechanical Shaker, Eberbach Inc.; Class A Volumetric Glass Containers, various sizes; API5000 Tandem Mass Spectrometer, Sciex, (Toronto, Canada); Turbo V™ Ion Source with APCI probe, Sciex, (Toronto, Canada); Aria TX4 HTLC System, Thermo Fisher Scientific, (MA, USA) consisting of 4 each: 1100 Series Quaternary Pump, 1100 Series Binary Pump, 1100 Series Vacuum Degasser; HTS Twin PAL System Autosampler, CTC Analytics AG (Switzerland); Synergi 4μ Fusion-RP 80 Column, 50×2.0 mm, Phenomenex, (USA) Product No. 00B-4424-B0; Vortex Mixer, VWR or equivalent; BIOMEK FX Automated Liquid Handling Device. Beckman Coulter, (CA, USA); Combi-thermo Heat Sealer, Abgene Inc., Product No. AB-0559; 96-Well Centrifuge 5804R Eppendorf or equivalent; 12×75 mm borosilicate glass tubes; Analyst Version 1.5 or greater. Applied Biosystems, (CA, USA); and Aria OS Version 1.5.1 or greater, Thermo Fisher Scientific (MA, USA).

The following reagents are used: Water—Type I, Millipore MilliQ or equivalent; Water—Type II, Redistilled in glass; Acetonitrile, HPLC grade (Fisher Scientific, Catalog #A998-4); Methanol, Certified A.C.S. (Fisher Scientific, Catalog #A408-4); Hexane, HPLC grade (Fisher Scientific, Catalog #H302-4); Ethyl Acetate, Optima (Fisher Scientific, Catalog #E196-4); Potassium Permanganate (EMD, Catalog #PM1550-1); Formic Acid (Sigma-Aldrich, Catalog #F0507); Ammonium Hydroxide (J. T. Baker, Reagent A. C. S. Catalog #9721-03); Dry ice bath, Container large and deep enough to immerse test tube rack, Prepare bath by immersing dry ice into methanol.

The following preparations are made: Pregnenolone Extraction Solvent (99.5:0.5 Hexane: Ethyl Acetate); In a 1 L flask add 995 mL Hexane and 5 mL Ethyl Acetate. Mix by shaking Store refrigerated. Expires after 6 months; 1% Potassium Permanganate Solution ($KMnO_4$); Dissolve and dilute 0.5 g of potassium permanganate ($KMnO_4$) with 50 mL of Type II redistilled water. Prepare fresh day of use. Discard immediately following use; Eluting Pump A Mobile Phase (90:5:5 Millipore Water: Methanol: Acetonitrile); Add 3600 mL of Type I Millipore water to 200 mL methanol and; 200 mL acetonitrile. Mix well. Store at room temperature. Expires after 6 months; Eluting Pump B Mobile Phase (45:45:10 Methanol: Acetonitrile: Millipore Water); Add 1800 mL methanol and 1800 mL acetonitrile to 400 mL Type I Millipore water. Mix well. Store at room temperature. Expires after 6 months; Internal Standard Solution ($D_4$-Pregnenolone at 3 ng/mL in Millipore Water with 1% Acetonitrile); Mix together 99 mL Millipore Type I water and 1 mL acetonitrile. Spike in 30 μL of 10 μg/mL D4-pregnenolone in ethanol. Mix well. Store refrigerated; Pregnenolone System Suitability Test (SST) Solution (500 pg/mL Pregnenolone in 70:30 Millipore Water: Methanol); In a 20 mL glass vial add 19.9 mL Pregnenolone Reconstitution Solution. Spike in 100 μL of 100 ng/mL pregnenolone in ethanol. Mix well. Store refrigerated; Pregnenolone Reconstitution Solution (70:30 Millipore Water: Methanol); Add 70 mL Millipore Water to 30 mL Methanol. Mix well. Store at room temperature. Expires after 6 months; Needle Wash Solution 1 (Aqueous 1% Formic Acid); Carefully in a fume hood, add 40 ml formic acid to 3560 mL Type I Water. Mix well. Store at room temperature. Expires after 6 months; Needle Wash Solution 2 (70:30 Acetonitrile: 1N Ammonium Hydroxide); Carefully in a fume hood, add 8 mL 15 N Ammonium Hydroxide and 2800 mL Acetonitrile to 1192 mL Type I Water. Mix well. Store at room temperature. Expires after 6 months.

Calibration

Calibrators are prepared from a stock solution of pregnenolone (10 μg/mL). Standards having the following concentrations (in ng/dL) are prepared: 10, 25, 50, 100, 250, 1000, and 2000. Standards are prepared by fortifying charcoal stripped serum at the concentrations listed above. Standards are stored for up to one year in polypropylene tubes when stored at <−20° C.

Procedure

Thaw and mix standards, samples and controls; Label three sets of 12×75 mm test tubes for each standard, control and patient; Unless otherwise directed, pipette 200 μL standard, control and patient into the first set of tubes with an Eppendorf pipette (or equivalent); Using an Eppendorf Plus repeating pipette with 5 ml tip (or equivalent), add 50 μL Internal Standard Solution to each tube except double blanks; Cover tubes with PARAFILM and mix all samples on multi-vortexer for 30 seconds; Add 2 mL 99.5:0.5 Hexane:Ethyl Acetate to all tubes; Cap tubes and place on mechanical shaker for 10 minutes; Spin down all samples in centrifuge up to 2000 rpm; Prepare 1% Potassium Permanganate Solution; Using an Eppendorf Plus repeating pipette with 10 mL tip (or equivalent), add 300 µL of 1% Potassium Permanganate Solution to each of the second set of labeled 12×75 mm tubes; Freeze aqueous layer of first set of extracted tubes in a dry ice bath and pour over into the corresponding second set of tubes containing the 1% Potassium Permanganate Solution; Cap tubes and place on mechanical shaker for 10 minutes; Spin down all samples in centrifuge up to 2000 rpm; After removing from centrifuge, remove and discard all caps; Freeze aqueous layer of second set of oxidized samples in a dry ice bath and pour over into the corresponding third set of fresh 12×75 mm test tubes; Place third set of 12×75 mm tubes in rotovap and dry for approximately 35 minutes at medium temperature setting; Remove samples from rotovap once there is no trace of solvent left in any tubes and add 120 µL of Pregnenolone Reconstitution Solution to each tube; Cover tubes with PARAFILM and mix on multi-vortexer 4×30 seconds; Transfer the entire volume of each reconstituted 12×75 mm tube to a 96-well plate using the BIOMEK FX Automated Liquid Handling Device or an Eppendorf pipette (or equivalent); Place a heat-sealing foil over the plate and seal the plate with the heated plate sealer; Centrifuge plate at 3700 rpm at 10° C. for 10 minutes; Place 96-well plate in LC-MS/MS Autosampler for subsequent LC-MS/MS analysis.

Example 2

Analysis of Pregnenolone Sample

The analysis method described in Example 1 was used to determine the pregnenolone levels in samples having standardized levels of pregnenolone. Table 1 below shows results for determinations of pregnenolone in spiked biological samples (pooled uman serum matrix (PN) and charcoal stripped human serum matric (S2)). For each biological sample, four different spiked concentrations were prepared: 0.000 added, 50.000 ng/dL added, 500.000 ng/dL added, and 1500 ng/dL added. For each combination of sample type and concentration, four measurements were recorded. The mean was recorded and compared to an expected amount.

TABLE 1

|  | Concentration Added (ng/dL) | | | |
| --- | --- | --- | --- | --- |
|  | 0.000 | 50.000 | 500.000 | 1500.000 |
|  | Concentration Measured (ng/dL) | | | |
| PN Low QC1 | 18.915 | 58.155 | 471.844 | 1407.427 |
|  | 16.885 | 59.186 | 504.061 | 1456.395 |
|  | 18.393 | 57.152 | 542.534 | 1447.743 |
|  | 18.993 | 58.656 | 516.084 | 1511.100 |
| Mean | 18.297 | 58.287 | 508.631 | 1455.666 |
| Expected Conc. | NA | 68.297 | 518.297 | 1518.297 |
| Recovery (%) | NA | 85.3 | 98.1 | 95.9 |
| n | 4 | 4 | 4 | 4 |
| S2 (25 ng/dL) | 23.029 | 67.083 | 498.156 | 1448.551 |
|  | 22.416 | 71.078 | 509.712 | 1545.353 |
|  | 22.562 | 69.901 | 526.243 | 1492.229 |
|  | 22.854 | 73.009 | 516.316 | 1511.351 |
| Mean | 22.715 | 70.268 | 512.607 | 1499.371 |
| Expected Conc. | NA | 72.715 | 522.715 | 1522.715 |
| Recovery (%) | NA | 96.6 | 98.1 | 98.5 |
| n | 4 | 4 | 4 | 4 |

We claim:

1. A method for determining the presence or amount of a delta 5 steroid compound in a sample, the method comprising:
    (a) providing a sample containing a delta 5 steroid compound and one or more delta 4 steroid compounds;
    (b) oxidizing the one or more delta 4 steroid compounds in the sample using an oxidizing agent;
    (c) chromatographically separating the delta 5 steroid compound from other components in the oxidized sample using liquid chromatography; and
    (d) analyzing the chromatographically separated delta 5 steroid compound by mass spectrometry to determine the presence or amount of the delta 5 steroid compound in the sample.

2. The method of claim 1, wherein the delta 5 steroid compound is pregnenolone, 17α-hydroxy-pregnenolone, or 5-dehydroepiandrosterone (DHEA).

3. The method of claim 1, wherein the one or more delta 4 steroid compounds are cortisol, 21-deoxycortisol, dexamethasone, corticosterone, beclomethasone, 11-desoxycortisol, triamcinolone acetonide, tetrahydrocortisol, 11-α-hydroxyprogesterone, tetrahydrocortisone, 19-nortestosterone, androstenedione, estradiol, estrone, 17a-ethynylestradiol, deoxycorticosterone, testosterone, 17α-hydroxyprogesterone, 17β-dihydroepiandrosterone, 17α methyltestosterone, budesonide, epiandrosterone, epitestosterone, dihydrotestosterone, dehydroandrosterone, fluticasone propionate, 20α-dihydroprogesterone, dihydroandrosterone, progesterone, 5α-androstan-3α-ol-17-one, 20β-hydroxyprogesterone, beclomethasone dipropionate, 5β-pregnane-3a,17a,20a-triol, pregnanolone, etiocholan-3α-diol, estriol, aldosterone, prednisone, cortisone, adrenosterone, 5α-androstan-3,11,17-trione, prednisolone, or pregnanediol.

4. The method of claim 1, where the oxidizing step (b) includes partitioning the delta 5 steroid compound and the one or more delta 4 steroid compounds between an aqueous phase and an organic phase, the aqueous phase comprising an oxidizing agent.

5. The method of claim 4, wherein the oxidizing agent is permanganate ion, chromate ion, osmium tetroxide, perchlorate ion, periodate ion, or any mixture of two or more of the foregoing.

6. The method of claim 4, wherein the organic phase comprises an organic water-immiscible solvent system.

7. The method of claim 6, where the organic water-immiscible solvent system comprises ethyl acetate, hexane, toluene, octanol, cholroform, dichloromethane, cyclohexane, pentane, N-heptanes, benzene, n-butyl chloride, butanol, methylene chloride or a mixture of two or more of the foregoing.

8. The method of claim 6 where the organic water-immiscible solvent system comprises an amount of at least one polar solvent, where the polar solvent is methanol, acetone, acetonitrile, isopropanol, diethyl ether, or methyl-tert-butyl ether.

9. The method of claim 1, wherein the oxidizing step (b) is carried out in an automated fashion.

10. The method of claim 1, wherein the oxidizing step (b) is carried out manually.

11. The method of claim 1, wherein using liquid chromatography includes using analytical liquid chromatography.

12. The method of claim 1, wherein using analytical liquid chromatography includes using a reverse phase column.

13. The method of claim 1, wherein the analyzing step (d) includes ionizing the delta 5 steroid compound using electrospray ionization, atmospheric pressure chemical ionization, or atmospheric pressure photoionization.

14. The method of claim 1, wherein the analyzing step (d) includes detecting the delta 5 steroid compound using a quadrupole mass spectrometer.

15. The method of claim 14, wherein the quadrupole mass spectrometer is a triple quadrupole mass spectrometer.

16. The method of claim 15, wherein the analyzing step (d) includes: detecting the intact delta 5 steroid compound ion in the first quadrupole; fragmenting the intact delta 5 steroid compound ion in the second quadrupole to yield one or more fragment ions; and detecting the one or more fragment ions in the third quadrupole.

17. The method of claim 1, where the analyzing step (d) includes determining the amount of the delta 5 steroid compound in the sample.

18. The method of claim 1, wherein the sample comprises an internal standard.

19. The method of claim 18, wherein the internal standard is a stable isotopically-labeled form of the delta 5 steroid compound.

20. The method of claim 19, wherein the stable isotopically-labeled form of the delta 5 steroid compound includes deuterium, carbon-13, or both.

21. The method of claim 20, wherein the internal standard is $D_4$-pregnenolone, $D_3$-17-hydroxy-pregnenolone, or $D_6$-5-dehydroepiandrosterone.

22. A method for determining the amount of a delta 5 steroid compound in a sample, the method comprising:
    (a) providing a sample containing a delta-5 steroid compound and one or more delta 4 steroid compounds;
    (b) oxidizing the one or more delta 4 steroid compounds in the sample using an oxidizing agent;
    (c) chromatographically separating the delta 5 steroid compound from the other components in the oxidized sample using reverse phase liquid chromatography; and
    (d) analyzing the chromatographically separated delta 5 steroid compound by mass spectrometry to determine the amount of the delta 5 steroid compound in the sample.

23. A method of generating a report useful for diagnosing a disease or condition associated with abnormal delta 5 steroid levels, the method comprising:
    (a) providing a sample containing a delta 5 steroid compound and one or more delta 4 steroid compounds;
    (b) oxidizing the one or more delta 4 steroid compounds in the sample using an oxidizing agent;
    (c) chromatographically separating the delta 5 steroid compound from other components in the oxidized sample using liquid chromatography;
    (d) analyzing the chromatographically separated delta 5 steroid compound by mass spectrometry to determine the presence or amount of the delta 5 steroid compound in the sample; and
    (e) generating a report that recites the concentration of a delta 5 steroid compound in the sample.

24. A system for determining the presence or amount of a delta 5 steroid compound in a sample, the system comprising:
    (a) a station for oxidizing a sample, the sample comprising a delta 5 steroid compound and one or more delta 4 steroid compounds;
    (b) a station for chromatographically separating the delta 5 steroid compound from other components in the oxidized sample using liquid chromatography; and
    (c) a station for analyzing the chromatographically separated delta 5 steroid compound by mass spectrometry to determine the presence or amount of the delta 5 steroid compound in the sample.

* * * * *